(12) United States Patent
Irvine et al.

(10) Patent No.: US 9,415,070 B2
(45) Date of Patent: Aug. 16, 2016

(54) METHODS AND COMPOSITIONS FOR LOCALIZED DELIVERY OF AGENTS TO VIRALLY INFECTED CELLS AND TISSUES

(71) Applicant: Massachusetts Institute of Technology, Cambridge, MA (US)

(72) Inventors: Darrell J. Irvine, Arlington, MA (US); Bruce D. Walker, Nahant, MA (US); Richard Bradley Jones, Toronto (CA)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/075,485

(22) Filed: Nov. 8, 2013

(65) Prior Publication Data
US 2014/0170221 A1    Jun. 19, 2014

Related U.S. Application Data

(60) Provisional application No. 61/724,771, filed on Nov. 9, 2012.

(51) Int. Cl.
| | |
|---|---|
| *A61K 35/14* | (2015.01) |
| *A61K 35/17* | (2015.01) |
| *A61K 38/20* | (2006.01) |
| *A61K 47/48* | (2006.01) |
| *A61K 31/167* | (2006.01) |
| *A61K 31/27* | (2006.01) |

(Continued)

(52) U.S. Cl.
CPC ............ *A61K 35/17* (2013.01); *A61K 31/167* (2013.01); *A61K 31/215* (2013.01); *A61K 31/27* (2013.01); *A61K 31/4045* (2013.01); *A61K 31/4406* (2013.01); *A61K 31/506* (2013.01); *A61K 31/675* (2013.01); *A61K 31/7068* (2013.01); *A61K 38/2086* (2013.01); *A61K 45/06* (2013.01); *A61K 47/48776* (2013.01); *A61K 47/48815* (2013.01); *A61K 47/48884* (2013.01); *A61K 47/48907* (2013.01); *A61K 47/48915* (2013.01); *A61K 9/127* (2013.01)

(58) Field of Classification Search
None
See application file for complete search history.

(56) References Cited

U.S. PATENT DOCUMENTS

| | | | |
|---|---|---|---|
| 8,816,122 B2 * | 8/2014 | Wender et al. ................. | 560/105 |
| 2007/0148246 A1 | 6/2007 | Luo et al. | |

(Continued)

FOREIGN PATENT DOCUMENTS

WO    WO 2010/059253 A2    5/2010

OTHER PUBLICATIONS

Fernadez et al. Cell line-dependent variability in HIV activation employing DNMT inhibitors, Virology Journal, 2010, 7:266.*

(Continued)

*Primary Examiner* — Robert A Wax
*Assistant Examiner* — Melissa Mercier
(74) *Attorney, Agent, or Firm* — Wolf, Greenfield & Sacks, P.C.

(57) ABSTRACT

The invention provides compositions and methods for delivering an agent to virally infected tissues and/or cells of a subject by conjugating agent-loaded nanoparticles to virus-specific T cells, such as cytotoxic T lymphocytes. The agent may be a latency-reversing drug (LRD), an antiviral agent and/or an agent that enhances cytotoxic efficacy of T lymphocytes.

20 Claims, 11 Drawing Sheets

(51) Int. Cl.
    *A61K 31/4045*     (2006.01)
    *A61K 31/4406*     (2006.01)
    *A61K 31/7068*     (2006.01)
    *A61K 31/506*     (2006.01)
    *A61K 31/675*     (2006.01)
    *A61K 45/06*     (2006.01)
    *A61K 31/215*     (2006.01)
    *A61K 9/127*     (2006.01)

(56) References Cited

U.S. PATENT DOCUMENTS

| | | | |
|---|---|---|---|
| 2008/0014144 | A1 | 1/2008 | Saltzman et al. |
| 2009/0035802 | A1 | 2/2009 | Chang et al. |
| 2010/0040589 | A1 | 2/2010 | Spetz-Holmgren et al. |
| 2010/0324034 | A1* | 12/2010 | Hazuda et al. .............. 514/230.5 |
| 2011/0229529 | A1* | 9/2011 | Irvine et al. .................... 424/400 |
| 2011/0229556 | A1 | 9/2011 | Irvine et al. |
| 2011/0293705 | A1* | 12/2011 | Irvine et al. .................... 424/450 |
| 2012/0177724 | A1 | 7/2012 | Irvine et al. |

OTHER PUBLICATIONS

Kovochich et al. Activation of Latent HIV using drug loaded nanoparticles, Plos One, Apr. 2011, vol. 6, Issue 4.*
Aline et al., Dendritic cells loaded with HIV-1 p24 proteins adsorbed on surfactant-free anionic PLA nanoparticles induce enhanced cellular immune responses against HIV-1 after vaccination. Vaccine. Aug. 20, 2009;27(38):5284-91. doi: 10.1016/j.vaccine.2009.05.028. Epub May 29, 2009.
Choi et al., Single chain variable fragment CD7 antibody conjugated PLGA/HDAC inhibitor immuno-nanoparticles: developing human T cell-specific nano-technology for delivery of therapeutic drugs targeting latent HIV. J Control Release. Nov. 30, 2011;152 Suppl 1:e9-10. doi: 10.1016/j.jconrel.2011.08.089.
Jones, Engineering the immune system to eradicate HIV. Nov. 11, 2012. Last accessed at http://conference.ohtn.on.ca/past-conferences/2012/presentations/plenary1b.pdf on Feb. 19, 2014.
Kovochich et al., Activation of latent HIV using drug-loaded nanoparticles. PLoS One. Apr. 5, 2011;6(4):e18270. doi: 10.1371/journal.pone.0018270.
Stephan et al., Therapeutic cell engineering with surface-conjugated synthetic nanoparticles. Nat Med. Sep. 2010;16(9):1035-41. doi: 10.1038/nm.2198. Epub Aug. 15, 2010.
Walker et al., T-Pharmacytes for the targeted eradication of HIV reservoirs. 2013. Last accessed at http://conference.ohtn.on.ca/past-conferences/2013/pdfs/183.pdf on Feb. 19, 2014.
Williams et al., Application of magnetic field hyperthermia and superparamagnetic iron oxide nanoparticles to HIV-1-specific T-cell cytotoxicity. Int J Nanomedicine. 2013;8:2543-54. doi: 10.2147/IJN.S44013. Epub Jul. 23, 2013.
Bershteyn et al., Polymer-supported lipid shells, onions, and flowers. Soft Matter. 2008;4(9):1787-1791.
Law et al., The structural basis for membrane binding and pore formation by lymphocyte perforin. Nature. Nov. 18, 2010;468(7322):447-51. doi: 10.1038/nature09518. Epub Oct. 31, 2010.
Shan et al., Stimulation of HIV-1-specific cytolytic T lymphocytes facilitates elimination of latent viral reservoir after virus reactivation. Immunity. Mar. 23, 2012;36(3):491-501. doi: 10.1016/j.immuni.2012.01.014. Epub Mar. 8, 2012.
Smith et al., HIV reservoirs and strategies for eradication. Curr HIV/AIDS Rep. Mar. 2012;9(1):5-15. doi: 10.1007/s11904-011-0108-2.
Stephan et al., Synapse-directed delivery of immunomodulators using T-cell-conjugated nanoparticles. Biomaterials. Aug. 2012;33(23):5776-87. doi: 10.1016/j.biomaterials.2012.04.029. Epub May 15, 2012.
Xing et al., Disulfiram reactivates latent HIV-1 in a Bcl-2-transduced primary CD4+ T cell model without inducing global T cell activation. J Virol. Jun. 2011;85(12):6060-4. doi: 10.1128/JVI.02033-10. Epub Apr. 6, 2011.
Pace et al., HIV reservoirs and latency models. Virology. Mar. 15, 2011;411(2):344-54. doi: 10.1016/j.virol.2010.12.041. Epub Feb. 1, 2011.

* cited by examiner

METHODS AND COMPOSITIONS FOR LOCALIZED DELIVERY OF AGENTS TO VIRALLY INFECTED CELLS AND TISSUES

RELATED APPLICATIONS

This application claims the benefit under 35 U.S.C. §119(e) of U.S. provisional application No. 61/724,771, filed Nov. 9, 2012, which is incorporated by reference herein in its entirety.

BACKGROUND OF THE INVENTION

An obstacle to treating certain viral infections, such as Human Immunodeficiency Virus (HIV), is the existence of a pool of infected resting memory $CD4^+$ T cells (Chun T W et al., *Nat Med* 1: 1284-90, 1995; Chun T W et al., *Nature* 387:183-88, 1997). Cells in this resting state do not produce virus and thus neither die by viral cytopathic mechanisms nor are they effectively targeted by the immune system. Upon cessation of antiviral therapy, these cells are thought to re-seed systemic infection, likely as a result of sporadic activation. The longevity of resting memory $CD4^+$ T cells, with a half-life of 44 months, renders this 'latent reservoir' an obstinate barrier to eradication.

SUMMARY OF THE INVENTION

The invention provides improved methods and compositions for more effectively treating viral infections associated with latency. The invention relates generally to the use of agent-loaded nanoparticles conjugated to virus-specific $CD8^+$ T lymphocytes (T cells) to deliver the agent to virally infected tissues/cells. More specifically, the nanoparticles are loaded with at least one a latency-reversing drug (LRD), an antiviral agent, an agent that enhances cytotoxic efficacy of the T cells, or any combination thereof, and are conjugated to virus-specific T cells (e.g., $CD8^+$ T cells that specifically target an epitope of a viral protein). Such cells are believed to be capable of homing to tissue sites where latently infected cells reside.

The invention is based, in part, on the discovery that the coordinated actions of LRDs and an immune response effectively eliminate cells latently infected with virus. The LRD, upon release from the nanoparticle at sites of viral infection, transiently activates (i.e., induces expression of) latent virus. In some instances, the LRD also stimulates cytotoxic activity of the virus-specific T cells, resulting in cell death and clearance of the infected cells. Agent-loaded nanoparticles conjugated to virus-specific $CD8^+$ T cells may be referred to herein as "T pharmacytes." A virus-infected cell may be referred to herein as a "target cell."

In various aspects and embodiments, the invention contemplates the use of nanoparticles conjugated to Human Immunodeficiency Virus (HIV)-specific T cells to deliver a LRD to HIV infected tissues/cells in a controlled and localized manner. When used in combination with antiviral agents, the present invention provides an efficient and effective way to eliminate cells that actively express HIV as well as reservoirs of latently infected cells.

Thus, in one aspect of the invention, provided herein are methods for delivering to an agent to virally infected cells, the methods comprising administering, to a subject having or suspected of having a viral infection, a virus-specific T cell bound to a nanoparticle that comprises an agent, wherein the agent is released from the nanoparticle in vivo. In some embodiments, the virally infected cells are HIV infected cells and the virus-specific T cells are HIV-specific T cells. As used throughout this disclosure, "a" or "an" means "at least one" or "one or more," unless otherwise indicated.

In some embodiments, the agent is a latency reversing drug (LRD). In some embodiments, the agent is an antiviral agent, for example, an antiretroviral agent. In some embodiments, the agent enhances cytotoxic efficacy of the virus-specific T cells.

In some embodiments, the methods further comprise administering to the subject antiretroviral therapy (ART) (e.g., a combination of at least two or at least three antiretroviral agents).

In another aspect of the invention, provided herein are virus-specific T cells bound to a nanoparticle that comprises a latency reversing drug (LRD), wherein the LRD is released from the nanoparticle in vivo. In some embodiments, the virus-specific T cells are HIV-specific T cells.

In some embodiments, the LRD is a histone deacetylase inhibitor (HDACi), a methylation inhibitor, a protein kinase C (PKC) modulator, or a cytokine. In some embodiments, the HDACi is vorinostat, panobinostat, entinostat or gavinostat. In some embodiments, the methylation inhibitor is 5-aza-2'deoxycitidine. In some embodiments, the PKC modulator is prostratin. In some embodiments, the cytokine is interleukin-15 or interleukin-15 superagonist (IL-15SA). In other embodiments, the LRD is not a cytokine, particularly not IL-15 or IL-15SA.

In some embodiments, the HIV-specific T cell is autologous to the subject.

In some embodiments, the HIV-specific T cell is activated prior to administration to the subject.

In some embodiments, the HIV-specific T cell is naturally occurring. In some embodiments, the HIV-specific T cell is genetically engineered (e.g., obtained from the subject and then genetically manipulated).

In some embodiments, the nanoparticle is about 20-500 nm in diameter, about 100-300 nm in diameter or about 150 nm in diameter. The invention also contemplates the use of microparticles (e.g., particles having a size of about 0.1 μm to about 100 μm) conjugated to T cells. For convenience, the term "nanoparticle(s)" is used to describe various aspects and embodiments of the invention. It is to be understood that the invention also contemplates the use of "microparticle(s)", unless otherwise indicated.

In some embodiments, the nanoparticle is covalently bound to the HIV-specific T cell.

In some embodiments, the nanoparticle is perforin-sensitive. As used herein, a "perforin-sensitive" nanoparticle permits perforin insertion and perforin complex assembly, as described elsewhere herein. For example, liposomes are herein considered to be perforin sensitive.

In some embodiments, a plurality of nanoparticles is bound to the HIV-specific T cell. In some embodiments, a plurality of nanoparticles is covalently bound to the HIV-specific T cell. In some embodiments, the plurality of nanoparticles comprises an identical agent. In some embodiments, the plurality of nanoparticles comprises different agents. In some embodiments, a single nanoparticle of the plurality of nanoparticles comprises more than one type of agent. In some embodiments, the plurality of nanoparticles is about 50 to about 500 nanoparticles.

In another aspect of the invention, provided herein are methods comprising contacting a virus-infected cell (such as a HIV-infected cell) with a virus-specific T cell (such as an HIV-specific T cell) that is bound to a nanoparticle that comprises an agent, wherein the agent is released from the nanoparticle. The method may be performed in vivo or in vitro. In some embodiments, the method may be used to screen for latency reversing drugs (LRDs) or other agents, including those that synergize with CTL immune responses.

These and other aspects and embodiments will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. In the drawings, each identical or nearly identical component illustrated in various figures is represented by a like numeral. For purposes of clarity, not every component may be labeled in every drawing.

DETAILED DESCRIPTION OF THE INVENTION

Figure 1:
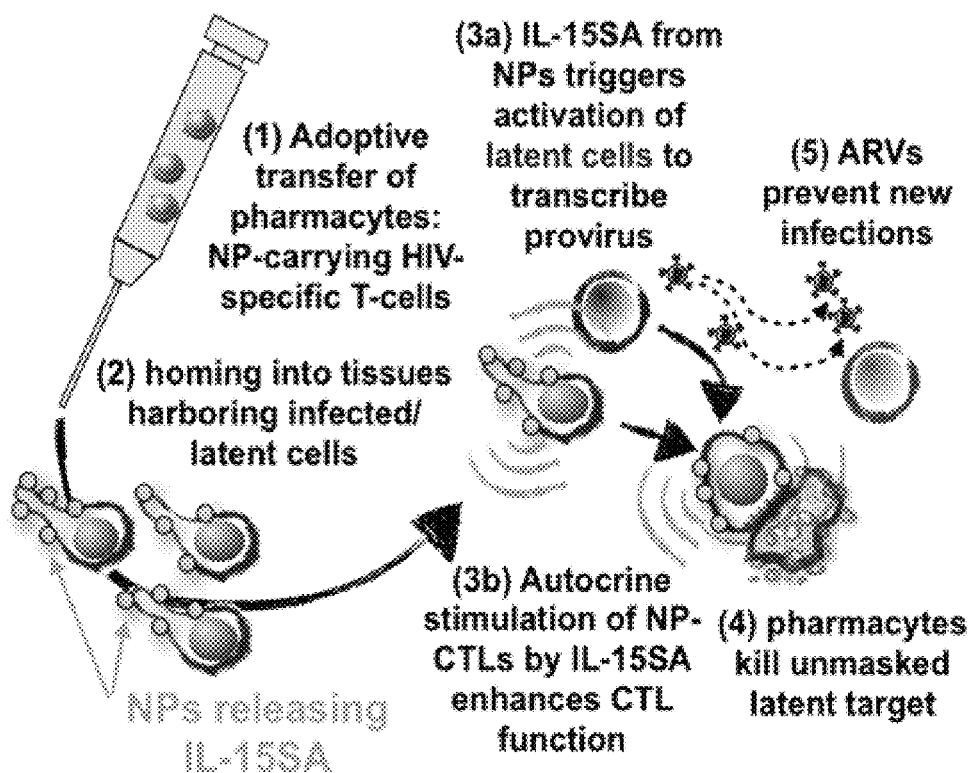
FIG. 1 shows a schematic depicting a non-limiting example of a method of the invention for systemic targeting of latent HIV reservoirs.

The invention contemplates, inter alia, in vivo delivery of virus-specific $CD8^+$ T cells conjugated to nanoparticles loaded with a latency-reversing drug (LRD), an antiviral agent, an agent that enhances cytotoxic efficacy of the T cells, or any combination thereof. Latency-reversing drugs induce expression of latent virus in infected cells and, in some instances, stimulate cytotoxic activity of their T cell carriers. Infected cells actively expressing virus are then targeted and eliminated by the virus-specific T cells. This delivery strategy involves the conjugation of nanoparticles that comprise a LRD (and/or other agents) to a cytotoxic T cell that can home specifically to virally infected cells in vivo, thereby resulting in localized and controlled delivery of the LRD in vivo.

The approach described herein offers significant advantages over prior art approaches of administering a LRD alone. Existing strategies for delivering a LRD to latently infected cells (e.g., in the absence of a carrier T cell) rely on the premise that the induction of latent viral expression in the cells results in cell death and clearance; however, reversal of viral latency, alone, is not sufficient to drive the death of infected cells (Shan L et al., *Immunity* 36: 1-11, 2012).

The invention exploits the use of nanoparticles and virus-specific T cells in the localized delivery of a LRD, typically in combination with antiviral therapy. The T cells function both as carriers that home to virally infected cells within the body, thereby delivering the LRD more specifically within the body to induce viral expression, and as a tool to eliminate the cells actively expression the virus. Examples of cells infected with latent virus include memory T cells (e.g., $CD4^+$ T cells), naïve T cells (e.g., $CD31^+$ $CD4^+$ T cells), hematopoietic progenitor cells, astrocytes, cells of the gastrointestinal tract, cells of the central nervous system, cells of lymphoid tissue, cells of the myeloid lineage including macrophages, and cells of the genitourinary tract (Smith et al., *Curr HIV/AIDS Rep,* 9:5-15, 2012).

In some embodiments, virus-specific T cells (e.g., HIV-specific T cells) are conjugated to nanoparticles, which are loaded with a LRD. As the LRD is released from the nanoparticles, it functions to induce viral expression in latently infected cells, thereby triggering activation of the T cells, which recognize and kill the infected cells. Examples of LRDs are provided elsewhere herein.

In some embodiments, the virus-specific T cells (e.g., HIV-specific T cells) may to be conjugated to a population of nanoparticles loaded with a latency-reversing drug (LRD), an antiviral agent, an agent that enhances cytotoxic efficacy of the T cells, or any combination thereof. In some embodiments, the virus-specific T cells may be conjugated to more than one population of nanoparticles, each loaded with a different agent. In yet other embodiments.

In some embodiments, more than one population of virus-specific T cells (e.g., HIV-specific T cells) are delivered, each population conjugated to nanoparticles loaded with a different type of agent (e.g., LRD or antiviral agent or agent that enhances cytotoxic efficacy of the T cells).

In some embodiments, a LRD, an antiviral agent, an agent that enhances cytotoxic efficacy of the T cells, or any combination thereof is delivered systemically (e.g., intravenously), in addition to or instead of delivery via nanoparticles. In some embodiments, a LRD, an antiviral agent, an agent that enhances cytotoxic efficacy of the T cells, or any combination thereof is delivered systemically to supplement the same and/or other agents delivered by nanoparticles conjugated to virus-specific T cells.

The Examples demonstrate the mechanism of action of the LRD that is a paracrine mechanism as well as an autocrine mechanism. The LRD carried by the nanoparticles functions on latently infected cells and/or tissues at the target site (i.e., a paracrine manner) as well as on the virus-specific T cell (e.g., HIV-specific T cell) carriers themselves (i.e., an autocrine manner).

Also demonstrated herein is a correlation among the amount of LRD encapsulated within the nanoparticle, the number of nanoparticles conjugated to a single virus-specific T cell, drug release kinetics, and the efficacy of viral latency reversal.

Various aspects and embodiments described herein are directed to Human Immunodeficiency Virus (HIV); however, it is to be understood that the invention extends to other viruses that demonstrate latency including, for example, cytomegalovirus (CMV), Epstein-Barr virus (EBV), herpes simplex virus-1 (HSV-1), herpes simplex virus-2 (HSV-2), human papilloma virus (HPV), rubella panencephalitis, varicella zoster virus (chickenpox), among others. For convenience and brevity, various aspects and embodiments are described in the context of "HIV". It is to be understood however that the invention contemplates such aspects and embodiments using other latency-demonstrating viruses, unless otherwise indicated.

The methods provided herein may be easily incorporated into any clinical process. The method requires simple mixing of the LRD-loaded nanoparticles with the virus-specific T cells. Nanoparticles can be prepared and stored in a convenient form prior to use (e.g., lyophilized powder or cryopreserved). Nanoparticles are then reconstituted in a suitable carrier and incubated with the HIV-specific T cell population for a brief period of time. Incubation times may range from 1-5 minutes, 1-10 minutes, 5-10 minutes, 5-15 minutes, 5-20 minutes, 5-30 minutes, or 5-60 minutes. The mixture is then washed, in some instances incubated with a blocking agent to quench the reactive groups on the nanoparticle and optionally on the T cell, washed again, and then formulated for administration. In some embodiments, the quenching agent is polyethylene glycol thiol (PEG-SH), which also serves to diminish antibody recognition of the nanoparticles. Administration typically will occur through parental routes such as, for example, intravenous injection.

Viral Latency

Viral latency, generally, is the ability of a pathogenic virus to lie dormant (i.e., latent) within a cell. In latently infected cells, the integrated provirus is transcriptionally silent (Hermankova M et al., *J Virol* 77: 7383-92, 2003; Chun T W et al., *Proc Natl Acad Sci USA* 100: 1908-13, 2003) but is able to produce replication-competent virus after cellular activation (Finzi, 1997; Wong, 1997; Chun, 1997). Thus, by reversing latency through induction of viral expression, the virus can reactivate and begin producing large amounts of viral progeny without the host being infected by new, outside virus.

Stable, latent reservoirs (cell populations) for viruses (e.g., HIV-1) exist among, for example, resting memory $CD4^+$ T cells (Chun, 1995, 1997; Finzi D et al., *Science* 278: 1295-1300, 1997; Wong J K et al., *Science* 278: 1291-95), and such reservoirs are a major barrier to viral eradication. Because of the stability of the reservoir (Siliciano J D et al., *J. Infect. Dis.* 195: 833-36, 2007; Strain M C et al., *Proc. Natl. Acad. Sci. USA* 100: 4819-24, 2003), life-long antiretroviral therapy is required, raising concerns about adverse effects over decades of therapy, the evolution of resistance, and the financial burden of treatment. The invention, therefore, contemplates methods of eradicating virus (e.g., HIV-1) from latently infected cells through the targeted and controlled delivery of latency reversing drugs in the context of an activated cytotoxic T cell virus-specific immune response, optionally in combination with short-term antiretroviral therapy.

Examples of viruses that may be targeted in accordance with the invention include, without limitation, cytomegalovirus (CMV), Epstein-Barr virus (EBV), herpes simplex virus-1 (HSV-1), herpes simplex virus-2 (HSV-2), human papilloma virus (HPV), rubella panencephalitis, and varicella zoster virus (chickenpox).

Virus-specific T Cells

As used herein, a "virus-specific T cell" is a cytotoxic $CD8^+$ T lymphocyte that specifically targets an epitope of a virus such as but not limited to an epitope on a viral protein. For example, HIV-specific $CD8^+$ T cells, when administered in vivo, specifically target (home to) an epitope of HIV-1 Gag protein. The virus-specific T cells are the cells to which agent-loaded nanoparticles are conjugated. These T cells can carry, but do not significantly internalize (e.g., endocytose), the nanoparticles. Further, substantial levels of free thiol (—SH) groups exist on the surfaces of T cells, thereby facilitating conjugation of nanoparticles to such cells.

Some embodiments of the invention refer to isolated T cells. Isolated T cells are cells that have been separated from the environment in which they naturally occur (i.e., they are not present in vivo). T cells in vitro are an example of an isolated cell.

The virus-specific T cells may be autologous to the subject being treated, or the virus-specific T cells may be non-autologous (yet preferably MHC matched cells).

The virus-specific T cells preferably have a half-life in vivo, following administration (or re-infusion, in some instances), of at least 48 hours, at least 3 days, at least 4 days, at least 5 days, at least 6 days, at least 1 week, at least 2 weeks, at least 3 weeks, at least 1 month, at least 2 months, at least 3 months, at least 4 months, at least 5 months or more.

The virus-specific T cells may be genetically engineered to express one or more factors including, without limitation, co-stimulatory molecules or receptors including engineered high avidity T cell receptors or chimeric antigen receptors. In other embodiments, the T cells are not genetically engineered. In some such embodiments, the T cells are isolated and naturally occurring (i.e., they have not been genetically engineered or otherwise engineered).

Depending on their nature and function, the virus-specific T cells may be manipulated prior to conjugation with the nanoparticles. The cells, however, need not be surface-modified in order to facilitate conjugation of the nanoparticles. The invention, in some embodiments, instead takes advantage of reactive groups that normally exist on the cell surface without having to incorporate reactive groups or other entities onto the cell surface. As a result, such cells do not require the presence of exogenous entities such as antibodies or antibody fragments, among others, on their surface in order to conjugate to nanoparticles.

Such manipulation may also involve activation of the virus-specific T cells, as is routinely performed for T cells. The cells may be expanded and/or activated (or stimulated, as the terms are used interchangeably herein) in vitro prior to mixing with the nanoparticles (or liposomes). Expansion and activation protocols can include incubation with at least one cytokine, incubation with at least one cell type, or incubation with at least one antigen. For example, activation may be performed by incubating the cells with IL-2, IL-15, IL-15 superagonist (IL-15SA), co-stimulatory molecules such as B7, B7.2, CD40, antibodies to various T cell surface molecules including antibodies to cell surface receptors, anti-CD3 antibodies, anti-CD28 antibodies, anti-CTLA-4 antibodies and/or anti-CD40L antibodies. In some embodiments, the T cells are not coated with exogenous antibodies on their cell surface (i.e., prior to administration the cells have not been contacted in vitro with antibodies or antibody fragments).

Expansion may be measured by proliferation assays involving incorporation of radiolabeled nucleotides such as tritiated thymidine. Activation may be measured by production of cytokines such as IL-2, gamma-IFN, IL-1, IL-4, IL-6, and TNF, among others. Other ways of measuring expansion and activation are known in the art.

Virus-specific T cells may be selected prior to conjugation to nanoparticles and/or prior to administration to a subject in order to enrich and thus administer higher numbers of such cells in smaller volumes and/or to remove other, potentially unwanted, cells from the administered composition. Selection may involve positive or negative selection including, for example, column or plate based enrichment protocols which are known in the art.

Virus-specific T cells may be harvested from the peripheral blood of a subject. Virus-specific T cells are preferably human cells.

Nanoparticles

As used herein, nanoparticles are particles of approximate nanometer dimensions capable of holding and releasing at least one agent.

In some embodiments, the nanoparticles are formed from polymers including, without limitation, aliphatic polyesters, poly (lactic acid) (PLA), poly (glycolic acid) (PGA), co-polymers of lactic acid and glycolic acid (PLGA), polycarprolactone (PCL), polyanhydrides, poly(ortho)esters, polyurethanes, poly(butyric acid), poly(valeric acid), and poly (lactide-co-caprolactone), and natural polymers such as alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof.

In some embodiments, the nanoparticles may comprise a lipid bilayer on their outermost surface. This bilayer may be comprised of one or more lipids of the same or different type. Examples include, without limitation, phospholipids such as phosphocholines and phosphoinositols. Specific examples include, without limitation, DMPC, DOPC, DSPC, DOPG and various other lipids.

In some embodiments, the nanoparticles are liposomes. Liposomes are vesicles comprising at least one lipid bilayer and an internal aqueous compartment. Liposomes may be anionic, neutral or cationic. Liposomes may comprise, without limitation, DOTMA, DOTAP, DOTIM, DDAB, alone or together with cholesterol, to yield DOTMA and cholesterol, DOTAP and cholesterol, DOTIM and cholesterol, and DDAB and cholesterol. In some embodiments, the nanoparticles of the invention may be unilamellar liposomal vesicles. In some embodiments, the nanoparticles of the invention may be multilamellar liposomal vesicles. In some embodiments, the nanoparticles may be interbilayer crosslinked multilamellar vesicles (ICMVs), which are multilamellar lipid vesicles having crosslinked lipid bilayers. Such nanoparticles are described in greater detail in U.S. application numbers US 2011/0229529 A1 and US 2012/0177724 A1, each of which is incorporated by reference herein.

In some embodiments, the nanoparticles may be biodegradable nanoparticles such as, for example, nanoparticles having a biodegradable polymer core and a lipid bilayer coat. In some embodiments, the polymer core may be poly(DL-lactide-co-glycolide) (PLGA). In some embodiments, the bilayer coat may comprise phosphocholine, phosphoglycerol and/or phosphoethanolamine. Such nanoparticles are described in greater detail in U.S. application number US 2008/0014144 A1, Bershteyn et al., Soft Matter, 4:1787-1787, 2008, published international application number WO 2010/059253, and published U.S. application number 2011/0229556 A1, and each of which is incorporated by reference herein.

In some embodiments, the nanoparticles may comprise a nucleic acid core and, optionally, a lipid coating. Such "DNA nanoparticles" or "DNA-hydrogel nanoparticles" are described in greater detail in published U.S. application number US 2007/0148246.

In some embodiments, the nanoparticles release the LRD (and/or antiretroviral agent) over a number of days. As discussed herein, in some embodiments, the nanoparticles are biodegradable in nature and thus they gradually degrade in an aqueous environment such as occurs in vivo. If the agents are dispersed throughout the nanoparticles, then their release will occur as the outermost layers of the nanoparticle degrade or as the pores within the nanoparticle enlarge. Release kinetic studies have demonstrated that protein and small-molecule drugs can be released from such nanoparticles over time-courses ranging from 1 day to at least 2 weeks. The nanoparticles are preferably not engulfed by either their HIV-specific T cells or other cells at the target site. They function rather by gradually releasing the agent into the environment of the target site(s).

In some embodiments, the nanoparticles release the agent all at once as the nanoparticle "bursts." For example, in some instances, when an HIV-specific T cell conjugated to a loaded nanoparticle encounters a HIV infected target cell, it moves into the immunological synapse (Stephan M T et al., Biomaterials 33(23): 5776-87, 2012). In the process of lysing the HIV infected target cell, the HIV-specific T cell might also lyse the nanoparticle thus releasing the agent in a "burst."

In some embodiments, the nanoparticle is sensitive to perforin. Natural killer cells and cytotoxic T lymphocytes kill virus-infected and neoplastic cells by releasing the pore-forming protein perforin and granzyme proteases from cytoplasmic granules into to the cleft formed between the abutting killer and target cell membranes. Perforin, a 67-kilodalton multidomain protein, oligomerizes to form pores that deliver the pro-apoptotic granzymes into the cytosol of the target cell (Tschopp et al. Nature 322, 831-834 (1986); Shinkai et al. Nature 334, 525-527 (1988); Lichtenheld et al. Nature 335, 448-451 (1988); Lowin et al. Nature 370, 650-652 (1994); Kagi et al. Nature 369, 31-37 (1994); and Young et al. Science 233, 184-190 (1986)). The present disclosure provides evidence that perforin released by activated T cells concomitantly triggers release of the contents of nanoparticles conjugated to the T cells (see, e.g., Examples 7-9). Thus, as used herein, a "perforin-sensitive" nanoparticle permits perforin-mediated pore formation in the nanoparticle such that pro-apoptopic granzymes can be delivered to the nanoparticle, thereby contributing to release of the agent loaded therein. Non-limiting examples of perforin-sensitive nanoparticles include liposomes and other nanoparticle with one or more lipid layers such as bilayers (e.g., fluid lipid bilayers). In some embodiments, such perforin-sensitive nanoparticles are not modified, or coated, with external moieties such as, for example, polyethylene glycol (PEG). Thus, in some embodiments, perforin-sensitive nanoparticles are not PEGylated. Such external moieties may prevent or hinder the insertion of perforin into the nanoparticle. It should be understood, however, that in some embodiments, the nanoparticles may be PEGylated, provided the degree of PEGylation does not interfere with perforin insertion into the nanoparticles.

The diameter of a nanoparticle typically ranges from 1-1000 nanometers (nm). In some embodiments, the diameter ranges in size from about 20 to 750 nm, from about 20 to 500 nm, or from about 20 to 250 nm. In some embodiments, the diameter ranges in size from about 50 to 750 nm, from about 50 to 500 nm, from about 50 to 250 nm, or from about 100-300 nm. In some embodiments, the diameter is about 100, about 150, about 200 nm, about 250 nm or about 300 nm. As used in the context of nanoparticle diameters, the term "about" means +/−5% of the absolute value stated. It is to be understood that although these particles are referred to herein as nanoparticles, the invention intends to embrace microparticles as well. For example, in some embodiments, the diameter of a microparticles may be used that range from 0.1 μm to 100 μm, 0.1 μm to 90 μm, 0.1 μm to 80 μm, 0.1 μm to 70 μm, 0.1 μm to 60 μm, 0.1 μm to 50 μm, 0.1 μm to 40 μm, 0.1 μm to 30 μm, 0.1 μm to 20 μm, 0.1 μm to 10 μm, 0.1 μm to 5 μm, 0.1 μm to 4 μm, 0.1 μm to 3 μm, 0.1 μm to 2 μm or 0.1 μm to 1 μm in diameter.

In some embodiments, the nanoparticles do not comprise antibodies or antibody fragments on their surface, while in other embodiments they do. In some embodiments, the nanoparticles do not comprise antibodies or antibody fragments that are specific to HIV-specific T cell surface moieties (or exogenous moieties coated onto a HIV-specific T cell surface such other antibodies or antibody fragments), while in other embodiments they do. Thus, in some embodiments the nanoparticles themselves do not stimulate HIV-specific T cell activation simply by binding to the T cell. In other embodiments, however, the nanoparticles do stimulate HIV-specific T cell activation by binding to the HIV-specific T cell (e.g., binding of the nanoparticle results in crosslinking of cell surface moieties and this activates the HIV-specific T cell).

The nanoparticles may be covalently conjugated (or attached or bound, as the terms are used interchangeably herein), or they may be non-covalently conjugated, to their carriers such as the HIV-specific T cells. Covalent conjugation typically provides a more stable (and thus longer) association between the nanoparticles and their carriers (such as HIV-specific T cells). Covalent conjugation, in some embodiments, can provide stability and thus more sustained localized delivery of LRDs (and/or antiretroviral agents) in vivo. Non-covalent conjugation includes, without limitation, absorption onto the cell surface and/or lipid bilayer of the cell membrane.

The nanoparticles may be synthesized or modified post-synthesis to comprise one or more reactive groups on their exterior surface for reaction with reactive groups on their carrier cells such as virus-specific T cells. These nanoparticle reactive groups include without limitation thiol-reactive maleimide head groups, haloacetyl (e.g., iodoacetyl) groups, imidoester groups, N-hydroxysuccinimide esters, pyridyl disulfide groups, and the like. As an example, nanoparticles may be synthesized to include maleimide conjugated phospholipids such as, without limitation, DSPE-MaL-PEG2000. These reactive groups react with groups on the surface of the carrier cell (such as a virus-specific T cell) and thus the nanoparticles are bound to the cell surface. It will be understood that when surface modified in this manner, the nanoparticles are intended for use with cells having "complementary" reactive groups (i.e., reactive groups that react with those of the nanoparticles). In some embodiments, the nanoparticles will not integrate into the lipid bilayer that comprises the T cell surface. Typically, the nanoparticles will not be endocytosed (or internalized) by the carrier cells (such as HIV-specific T cells).

In some embodiments, covalent attachment can be achieved in a two-step process in which for example T cells such as HIV-specific T cells are first incubated with maleimide-bearing nanoparticles to allow conjugation to the cell surface, followed by in situ PEGylation with thiol-terminated poly(ethylene glycol) (PEG) to cap remaining maleimide groups of the particles and avoid particle-mediated crosslinking of cells. With this approach, substantial numbers of nanoparticles with diameters in the 100-300 nm range have been conjugated to, for example, $CD8^+$ T lymphocytes. This strategy allows particles ranging from simple liposomes (e.g., with an aqueous drug-loaded core) to more complex lipid-coated polymer or DNA-based nanoparticles to be stably attached to live cells. It has been shown that the linkage chemistry is benign and non-toxic as evidenced in part by the conjugation of about 150 lipid-coated nanoparticles having a ~200 nm-diameter to the surface of cells without any deleterious effect.

Although liposomes and lipid-coated polymer particles are able to spontaneously adsorb to cell surfaces, in some instances covalent conjugation of nanoparticles may be preferred due to the increased stability it achieves.

It is to be understood that the nanoparticles may be conjugated to the HIV-specific T cells in vitro or in vivo.

In some embodiments, a plurality of nanoparticles is conjugated (e.g., covalently bound) to a carrier cell such as an HIV-specific T cell. In some embodiments, the plurality of nanoparticles is 50-10000, or 100-10000. In some embodiments, the plurality of nanoparticles is about 100, about 150, about 200, about 250 or about 500. In some embodiments, the plurality of nanoparticles is less than 100. For example, the plurality of nanoparticles may be about 90, about 80, about 70, about 60, about 50, about 40, about 30, about 20, 19, 18, 17, 16, 15, 14, 13, 12, 11, 10, 9, 8, 7, 6, 5, 4, 3 or 2.

In some embodiments, the concentration of the agent encapsulated in a nanoparticle may be about 10 μg/ml to about 100 mg/ml. For example, the concentration of the agent encapsulated in a nanoparticle may be about 10 μg/ml, about 20 μg/ml, about 30 μg/ml, about 40 μg/ml, about 50 μg/ml, about 60 μg/ml, about 70 μg/ml, about 80 μg/ml, about 90 μg/ml, about 100 μg/ml, about 150 μg/ml, about 200 μg/ml, about 250 μg/ml, about 300 μg/ml, about 350 μg/ml, about 400 μg/ml, about 450 μg/ml, about 500 μg/ml, about 550 μg/ml, about 600 μg/ml, about 650 μg/ml, about 700 μg/ml, about 750 μg/ml, about 800 μg/ml, about 850 μg/ml, about 900 μg/ml, about 950 μg/ml, about 1 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml or about 100 mg/ml.

In some embodiments, the invention contemplates the use of a low concentration of agent with few nanoparticles conjugated to HIV-specific T cells. For example, the concentration of LRD (and/or antiretroviral agent) incorporated into each nanoparticle may be about 100 μg/ml, and only about 100 nanoparticles may be conjugated to HIV-specific T cell.

In some embodiments, the amount of agent encapsulated in a nanoparticle may be about 0.1 ng to about 10 mg, about 0.1 ng to about 1 μg, or about 0.1 ng to about 100 ng.

Latency-reversing Drugs (LRDs)

The invention contemplates the delivery of latency-reversing drugs (LRDs) to virally infected tissues/cells in vivo. As used herein, a latency-reversing drug is any atom or molecule or compound that can be used to induce expression of a virus. The term "agent," as used herein, encompasses LRDs. Many of the agents listed below may also be used to enhance the cytotoxic efficacy of T cells.

Examples of LRDs include, without limitation, histone deacetylase inhibitors, methylation inhibitors, protein kinase C (PKC) modulators, and cytokines.

Histone deacetylase inhibitors. Histone deacetylase inhibitors are a class of compounds that interfere with the function of histone deacetylase. The classical histone deacetylase inhibitors act exclusively on Class I and Class II histone deacetylases (HDACs) by binding to the zinc-containing catalytic domain of HDACs. These classical histone deacetylase inhibitors fall into several groupings, in order of decreasing potency: hydroxamic acids (or hydroxamates) such as trichostatin A; cyclic tetrapeptides (such as trapoxin B) and the depsipeptides; benzamides; electrophilic ketones; and the aliphatic acid compounds such as phenylbutyrate and valproic acid.

"Second-generation" histone deacetylase inhibitors include hydroxamic acids (e.g., vorinostat (suberoylanilide hydroxamic acid, SAHA, Archin N M et al., *AIDS Res Hum Retroviruses,* 25(2): 207-12, 2009; Contreras X. et al. *J Biol Chem,* 284:6782-9, 2009), belinostat (PXD101), LAQ824 and panobinostat (LBH589) and benzamides (e.g., entinostat (MS-275), CI994 and mocetinostat (MGCD0103).

Other examples of histone deacetylase inhibitors for use in accordance with the invention include 4SC-202, abexinostat, ACTR, ACY-1215, AR-42, belinostat, CG200745, CHR-2845, CHR-3996, cMyb, CUDC-101, E2F1, EKLF, entinostat, FEN 1, GATA, givinostat, HNF-4, HSP90, kevetrin, Ku70, mocetinostat, NF-κB, p53, panobinostat, PCNA, RB, resminostat, romidepsin, runx, SB939, SF1 Sp3, STAT, sulforaphane, TCF, TFIIE, trichostatin A (TSA), YY1, trichostatin B, trichostatin C, trapoxin A, trapoxin B, chlamydocin, sodium salts of butyrate (sodium butyrate), butyric acid, sodium salts of phenylbutyrate, phenylbutyric acid, scriptaid, FR901228, depudecin, oxamflatin, pyroxamide, apicidin B, apicidin C, Helminthsporium carbonum toxin, 2-amino-8-oxo-9,10-epoxy-decanoyl, 3-(4-aroyl-1H-pyrrol-2-yl)-N-hydroxy-2-propenamide, suberoylanilide hydroxamic acid, FK228 or m-carboxycinnamic acid bis-hydroxamide, ITF2357 (Matalon S et al., *J Acquir Immune Defic Syndr.* 54: 1-9, 2010), CG05 and CG06 (Choi B-S et al., *AIDS* 24: 609-11, 2010), MCT-1 and MCT-3 (Shehu-Xhilaga M. et al., *AIDS* 23(15): 2047-50, 2009), NHC-51(Victoriano AFB et al., *FEBS Lett* 585: 1103-11, 2011), (Ylisastigui L et al., *AIDS* 18: 1101-08, 2004), disulfiram (Xing S et al., *J Virol* 85: 6060-64, 2011) and any of the histone deacetylase inhibitor compounds disclosed in Archin M N et al., *AIDS* 2009; 1799-806, incorporated by reference herein.

Methylation inhibitors. Methylation inhibitors inhibit DNA methylation, for example, by inhibiting DNA methyltransferase activity. Examples of methylation inhibitors for use in accordance with the invention include, without limitation, DNMTi 5-aza-2'deoxycitidine(5-aza-dc) (Fernandez G et al., *Virology J.* 7: 266, 2012), decitabine, DL-ethionine, D-methionine, 5-azacytidine, 5-aza-2'deoxycytidine, 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine, and procainamide, Zebularine and (−)-egallocatechin-3-gallate.

Protein Kinase C (PKC) Modulators. PKC modulators are agents that activate or inhibit PKC activity. Examples of PKC modulators for use in accordance with the invention include, without limitation, prostratin (Kulkosky J, *Blood* 98: 3006-15, 2001), bryostatin and rottlerin (Kovochich M et al., *PLoS One* 6: e18270, 2011), isoquinoline sulfonamide H-7 and its analogs (Hidaka H et al., *Biochemistry* 23: 5036, 1984), 4-aminomethyl-1-[2,3-(di-n-decyloxy)n-propyl]-4-phenylpiperidine (Shoji et al., *Biochem Biophys Res Commun* 234:590, 1985), phenothiazine agents (Mori T, et al., *J Biol Chem* 255: 8378, 1980; Schatzman R et al., *Biochem Biophys Res Commun* 98: 669, 1981), tamoxifen (O'Brien C, et al., *Cancer Res* 45: 2462, 1985), quercetin (Srivastava A, *Biochem Biophys Res Commun* 131: 1, 1985), amiloride (Besterman J, et al., *J Biol Chem* 260: 1155, 1985), verapamil (Mori T, et al., *J Biol Chem* 255: 8378, 1980), adriamycin (Wise, B et al., *J Biol Chem* 257: 8489, 1982), polymyxin B (Mazzei G, et al., *Biochem Biophys Res Commun* 109:1129, 1982), gangliosides (Kim J, *Neurosci Res* 15: 159, 1986), sangivamycin (Loomis C et al., *J Biol Chem* 263: 1682, 1988), retinal (Patarroyo, *Immunobiol* 170: 305, 1985), staurosporine (Tamoki T et al., *Biochem Biophys Res Commun* 135:397, 1986), aminoacridines (Hannum Y et al., *J Biol Chem* 263: 5124, 1988), sphingosine and related sphingolipids (Bell R et al., *Cold Spr Harbor Sym Quant Biol* 53: 103, 1988).

Cytokines. Cytokines are small cell-signaling protein molecules secreted by cells. HIV-inductive cytokines include TNF-α, TNF-β, IL-1 and IL-6, which stimulate HIV-1 replication in T cells and monocyte-derived macrophages (MDM), IL-2, IL-7 and IL-15/IL-15SA, which upregulate HIV-1 in T cells, and macrophage-colony stimulating factor, which stimulates HIV-1 in MDM (Kedzierska K et al., *Antivir Chem Chemother* 12(3): 133-50. Other examples of cytokines that may be used in accordance with the invention include Acrp30, AgRP, amphiregulin, angiopoietin-1, AXL, BDNF, bFGF, BLC, BMP-4, BMP-6, b-NGF, BTC, CCL28, Ck beta 8-1, CNTF, CTACK CTAC, Skinkine, Dtk, EGF, EGF-R, ENA-78, eotaxin, eotaxin-2, MPIF-2, eotaxin-3, MIP-4-alpha, Fas Fas/TNFRSF6/Apo-1/CD95, FGF-4, FGF-6, FGF-7, FGF-9, Flt-3 Ligand fms-like tyrosine kinase-3, FKN or FK, GCP-2, GCSF, GDNF Glial, GITR, GITR, GM-CSF, GRO, GRO-α, HCC-4, hematopoietic growth factor, hepatocyte growth factor, I-309, ICAM-1, ICAM-3, IFN-γ, IGFBP-1, IGFBP-2, IGFBP-3, IGFBP-4, IGFBP-6, IGF-I, IGF-I SR, IL-1α, IL-1β, IL-1, IL-1 R4, ST2, IL-3, IL-4, IL-5, IL-6, IL-8, IL-10, IL-11, IL-12 p40, IL-12p70, IL-13, IL-16, IL-17, I-TAC, alpha chemoattractant, lymphotactin, MCP-1, MCP-2, MCP-3, MCP-4, M-CSF, MDC, MIF, MIG, MIP-1α, MIP-1β, MIP-1δ, MIP-3α, MIP-3β, MSP-a, NAP-2, NT-3, NT-4, osteoprotegerin, oncostatin M, PARC, PDGF, P1GF, RANTES, SCF, SDF-1, soluble glycoprotein 130, soluble TNF receptor I, soluble TNF receptor II, TARC, TECK, TGF-beta 1, TGF-beta 3, TIMP-1, TIMP-2, TNF-α, TNF-β, thrombopoietin, TRAIL R3, TRAIL R4, uPAR, VEGF and VEGF-D.

Other LRDs. Examples of other compounds that activate latent HIV infection for use in accordance with the invention include, without limitation, AV6 (Micheva-Viteva S et al., *J Biol Chem.* 286(24): 21083-91, 2011), HIV-1-reacting protein factor (HRF) (Wolschendorf F et al., *J Virol.* 84: 8712-20, 2010) and disulfiram (Xing S et al., *J or Virol* 85(12): 6060-64).

The invention also contemplates the delivery of agents that eliminate latency indirectly by interfering with biological pathways that maintain latency.

Antiviral Therapy

The invention contemplates combination therapies including, for example, delivering the T pharmacytes of the invention to activate virus (e.g., HIV) in latently infected cells and to clear the cells, as described herein, and administering antiviral therapy (e.g., antiretroviral therapy) to prevent new HIV infection. Standard antiretroviral therapy includes the combination of typically three or more antiretroviral drugs to suppress, for example, HIV and to stop disease progression. Examples of antiretroviral drugs for use in accordance with the invention include, without limitation, nucleoside reverse transcriptase inhibitors (NRTIs), non-nucleoside reverse transcriptase inhibitors (NNRTIs), protease inhibitors, fusion inhibitors and entry inhibitors.

Examples of NRTIs include, without limitation, COMBIVIR® (lamivudine and zidovudine; GlaxoSmithKline), EMTRIVA® (emtricitabine; FTC Gilead Sciences), EPIVIR® (lamivudine, 3TC; GlaxoSmithKline), EPZICOM® (abacavir and lamivudine; GlaxoSmithKline), HIVID® (zalcitabine, dideoxycytidine, ddC; Hoffmann-La Roche), RETROVIR® (zidovudine, azidothymidine; GlaxoSmithKline), STRIBILD™ (tenofovir, disoproxil, fumarate; Gilead Sciences, Inc.), TRIZIVIR® (abacavir, zidovudine, lamivudine; GlaxoSmithKline), TRUVADA® (tenofovir, disoproxil, fumarate, emtricitabine; Gilead Sciences, Inc.), VIDEX® (EC11 enteric coated didanosine; Bristol Myers-Squibb), VIDEX® (didanosine, dideoxyinosine; Bristol Myers-Squibb), VIREAD® (tenofovir disoproxil fumarate; Gilead Gilead Sciences, Inc.), ZERIT® (stavudine; Bristol Myers-Squibb) and ZIAGEN® (abacavir sulfate; GlaxoSmithKline).

Examples of NNRTIs include, without limitation, EDURANT® (rilpivirine; Tibotec Therapeutics), INTELENCE® (etravirine; Tibotec Therapeutics), RESCRIPTOR® (delavirdine; Pfizer), SUSTIVA® (efavirenz; Bristol Myers-Squibb), VIRAMUNE® (nevirapine; Boehringer Ingelheim) and VIRAMUNE® XR21 (nevirapine; Boehringer Ingelheim).

Examples of protease inhibitors include, without limitation, AGENERASE® (amprenavir; GlaxoSmithKline), APTIVUS® (tipranavir; Boehringer Ingelheim), CRIXIVAN® (indinavir; Merck), FORTOVASE® (saquinavir; Hoffmann-La Roche), INVIRASE® (saquinavir mesylate; Hoffmann-La Roche), KALETRA® (lopinavir, ritonavir; Abbott Laboratories), LEXIVA® (Fosamprenavir Calcium; GlaxoSmithKline), NORVIR® (ritonavir; Abbott Laboratories), PREZISTA® (darunavir; Tibotec, Inc.), REYATAZ® (atazanavir sulfate; Bristol-Myers Squibb) and VIRACEPT® (nelfinavir mesylate; Agouron Pharmaceuticals).

Examples of fusion inhibitors include, without limitation, FUZEON® (viroc; Pfizer), SELZENTRY® (maraviroc; Pfizer) and ISENTRESS® (raltegravir; Merck & Co., Inc.).

An example of an entry inhibitor includes, without limitation, SELZENTRY® (maraviroc; Pfizer).

It is to be understood that the invention also contemplates administration of one, two, three or more antiviral agents in combination with the methods provided herein. For example, combination treatments such as COMPLERA® (emtricitabine/rilpivirine/tenofovir disoproxil fumarate; Gilead Gilead Sciences, Inc.) and ATRIPLA® (efavirenz, emtricitabine, tenofovir disoproxil fumarate; Gilead Gilead Sciences, Inc.) may be used in accordance with the invention.

Effective Amounts, Regimens, Formulations

In some embodiments, the agents provided herein may be administered in effective amounts. An effective amount is a dosage of the agent sufficient to provide a medically desirable result. For example, in instances where tissues/cells latently infected with HIV are being targeted, an effective amount of an LRD may be an amount effective to induce viral expression in the latently infected cells. The effective amount will vary with the particular virus being treated, the age and physical condition of the subject being treated, the severity of the condition, the duration of the treatment, the nature of the concurrent or combination therapy (if any), the specific route of administration and like factors within the knowledge and expertise of the health practitioner. It is preferred, generally, that a maximum dose be used (i.e., the highest safe dose according to sound medical judgment).

The invention provides compositions, including pharmaceutical compositions, comprising the T pharmacytes of the invention. Compositions may comprise cells, nanoparticles and/or agents. Pharmaceutical compositions are compositions that may comprise cells, nanoparticles and/or agents, preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and LRDs (and/or antiretroviral agents) are combined to facilitate administration. The components of the pharmaceutical compositions are commingled in a manner that precludes interaction that would substantially impair their desired pharmaceutical efficiency.

The compositions of the invention, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides.

EXAMPLES

Example 1

T Pharmacyte Delivery of Cytokines in a Paracrine Manner

Figure 2:
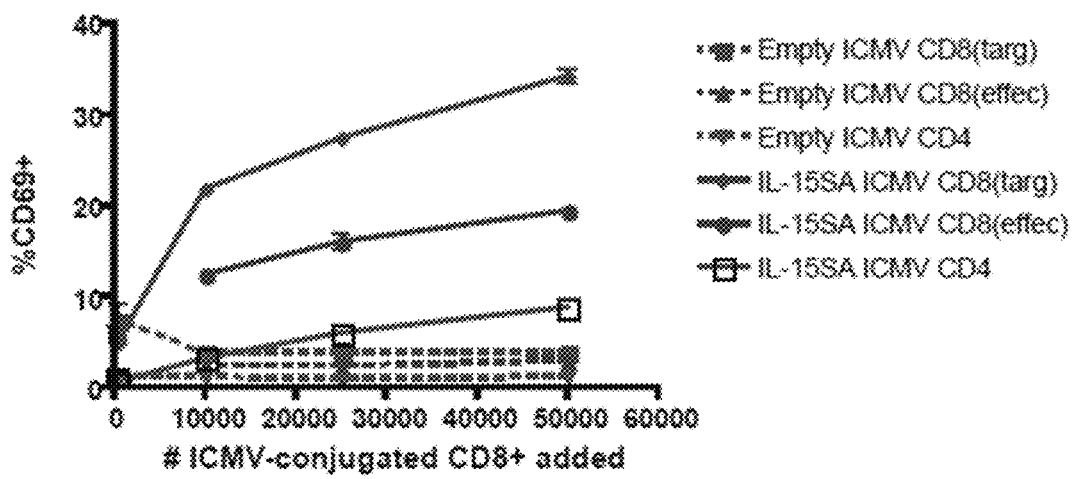
FIG. 2 shows a graph of data demonstrating that T pharmacytes of the invention effectively stimulate cells in a paracrine manner.

The experiment presented in this Example was directed to determining if T pharmacytes of the invention could effectively deliver cytokines to other cells (paracrine). T pharmacytes conjugated to nanoparticles loaded with 100 µg/ml of IL-15SA (superagonist) were co-cultured in vitro with unconjugated T cells. Surprisingly, of the two cell populations, the unconjugated T cells (FIG. 2, IL-15SA ICMV CD8 (targ)) were stimulated more efficiently than the T pharmacytes (IL-15SA ICMV CD8(effec)), demonstrating that the T pharmacytes can induce HIV expression in a paracrine manner.

Example 2

T Pharmacyte Induction of HIV Expression

Figure 3:
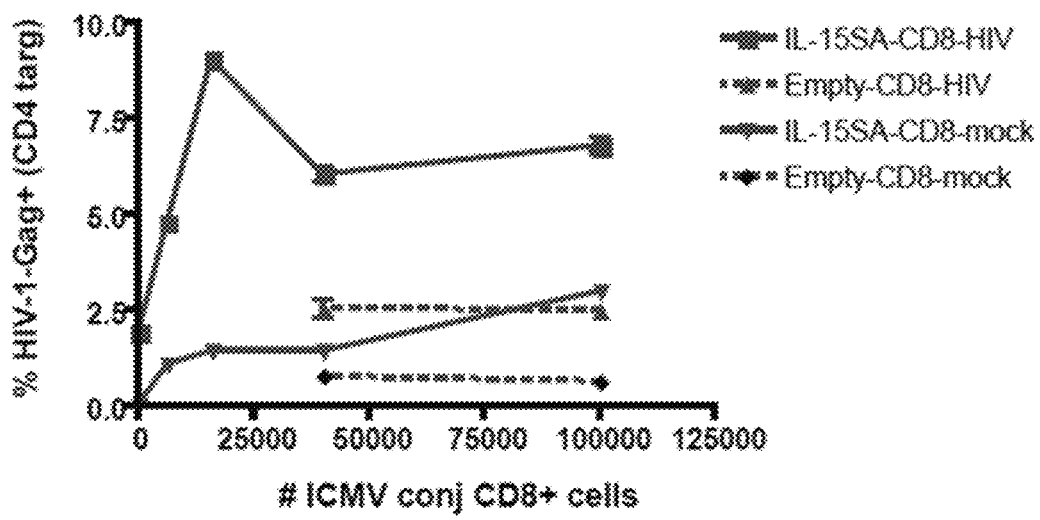
FIG. 3 shows a graph of data demonstrating that T pharmacytes of the invention induce expression of latent Human Immunodeficiency Virus (HIV)

The protein induction assay presented in this Example was directed to determining if the paracrine signaling demonstrated in Example 1 would induce HIV expression from latently infected resting CD4+ T cells. CD4+ T cells were co-cultured with T pharmacytes conjugated to nanoparticles (e.g., interbilayer-crosslinked multilamellar vesicles, ICMV; see publication numbers US 2011/022959 A1 and US 2011/0229556 A1, each of which is incorporated by reference herein) loaded with (a) IL-15SA or (b) not loaded (negative control). Clear induction of Gag expression was observed in CD4+ T cells co-cultured with T pharmacytes conjugated to nanoparticles loaded with IL-15SA, but not in CD4+ T cells co-cultured with the negative control (FIG. 3). Gag protein is among the most immunogenic proteins during HIV infection and is indicative of HIV expression.

Example 3

In vitro Eradication Assay

Figure 4:
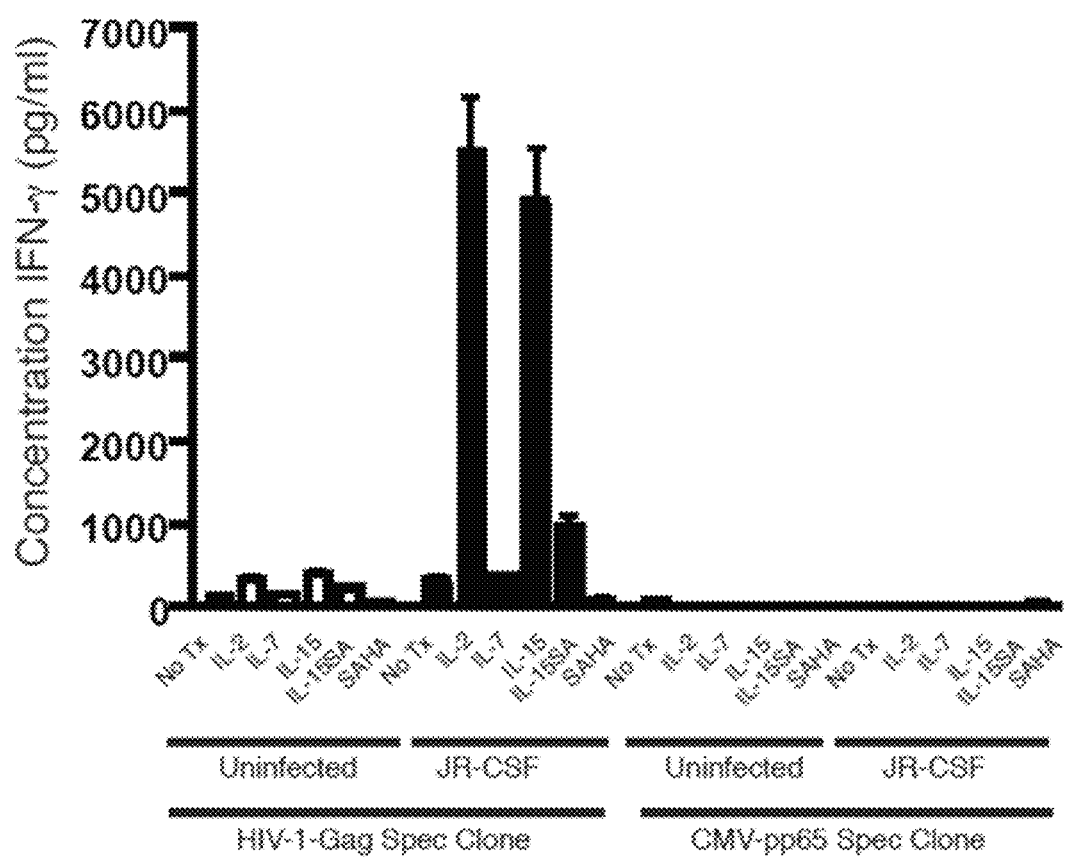
FIG. 4 shows a graph of data validating an in vitro eradication assay.

The in vitro cell eradication assay presented in this Example was directed to determining if T pharmacytes can induce expression of HIV expression in latently infected cells and kill those cells. HIV-specific T cells and Cytomegalovirus (CMV)-specific T cells were co-cultured with infected target cells (and mock-infected target cells) without the addition of any exogenous cytokines. The HIV-specific T cells specifically respond to these infected target cells only in the presence of latency reversing drugs (LRD) such as, for example, IL-2 and IL-15 (FIG. 4).

Example 4

In Vitro Eradication Assay

An in vitro cell eradication assay, analogous to the one above, was conducted in this Example.

Figure 5:
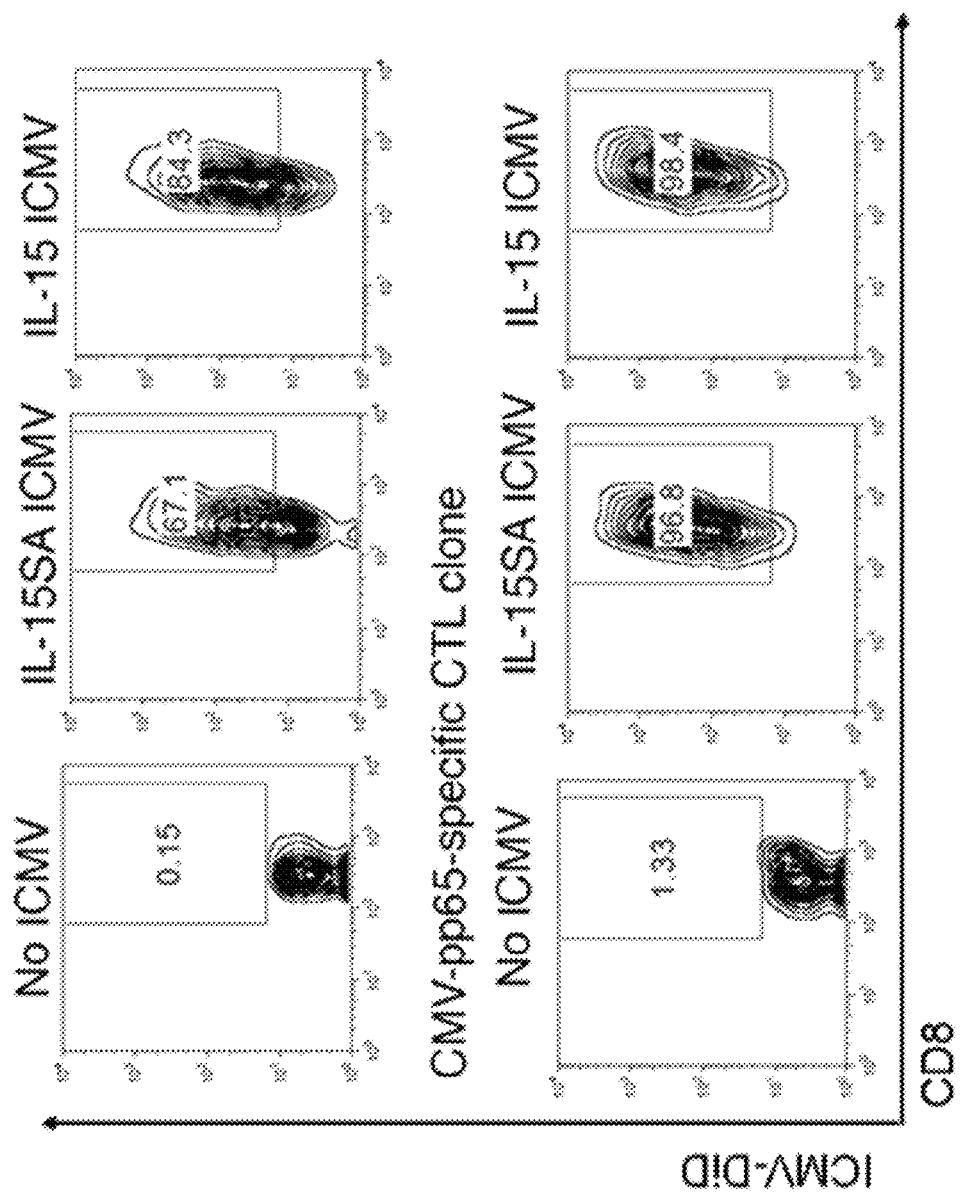
FIG. 5 shows graphs from a flow cytometry analysis demonstrating conjugation of nanoparticles to HIV- and Cytomegalovirus (CMV)-specific T cells.
Figure 5:
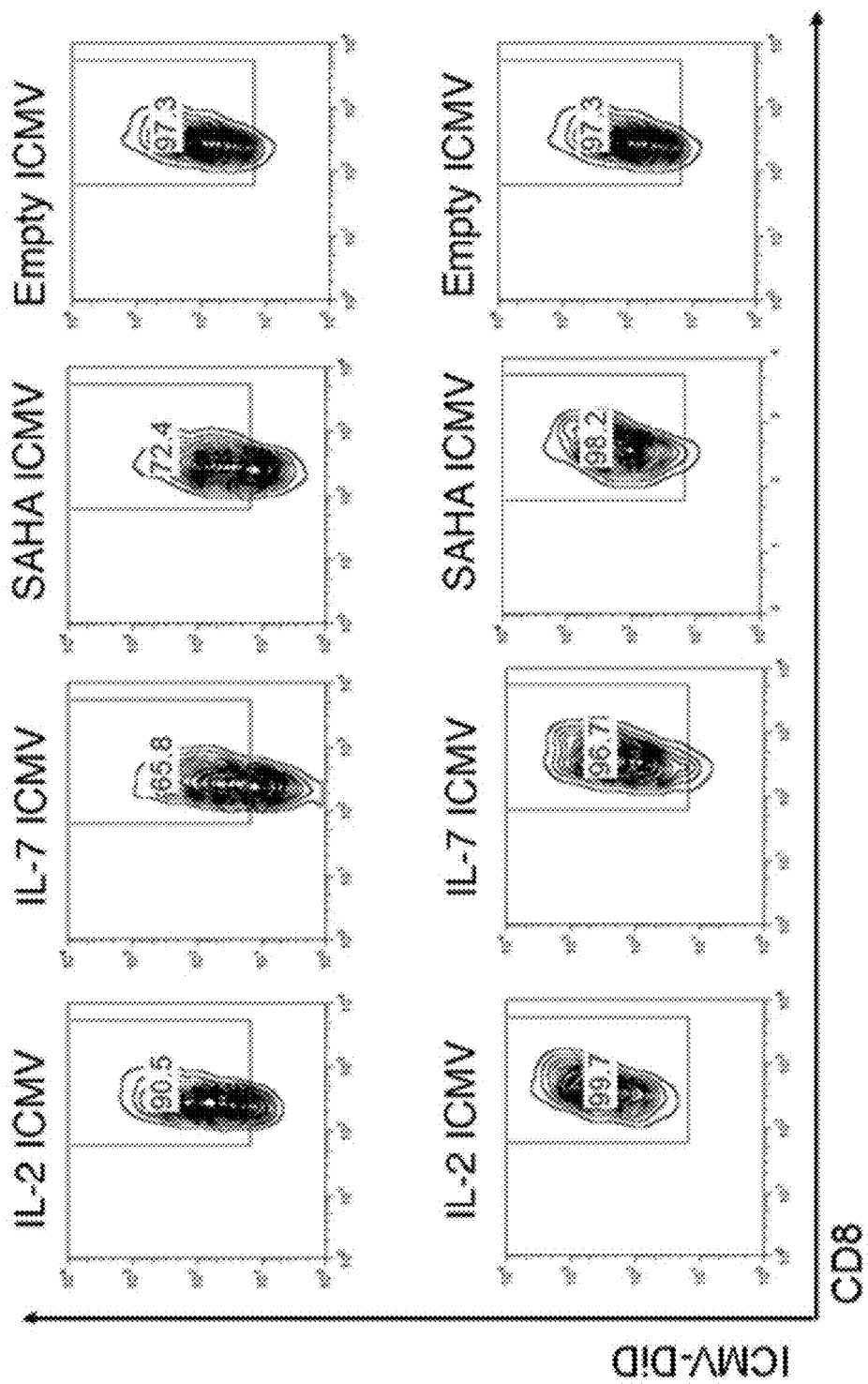
Figure 6:
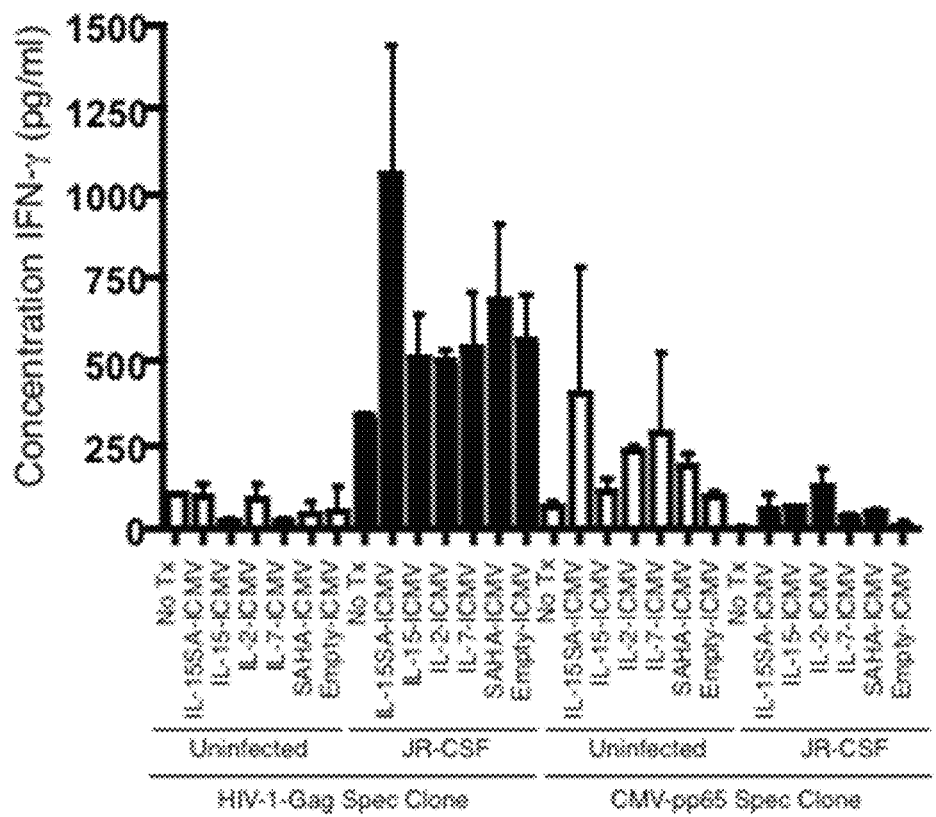
FIG. 6 shows a graph of data quantifying interferon-gamma (IFN-γ) production by T pharmacytes following three days of co-culture with target cells.
Figure 7:
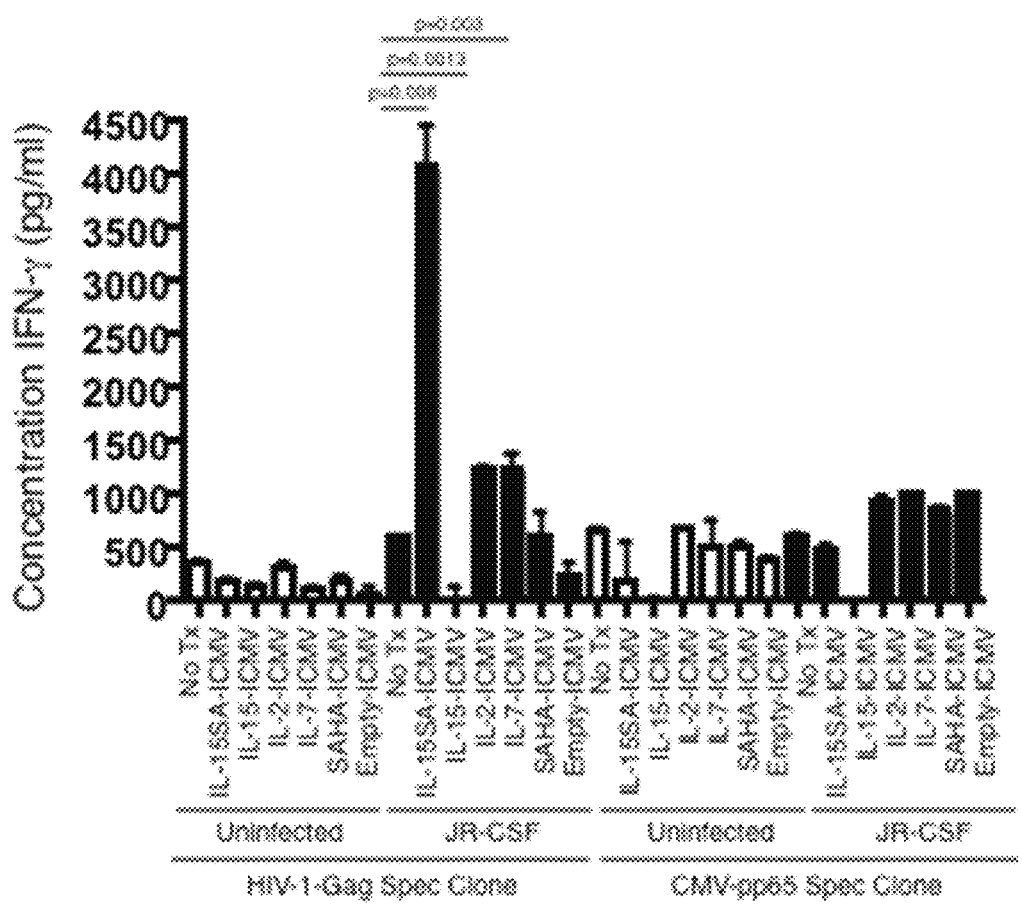
FIG. 7 shows a graph of data quantifying IFN-γ production by T pharmacytes following seven days of co-culture with target cells.

Conjugation of fluorophore (DiD) labeled nanoparticles to the HIV-specific T cells and to CMV-specific T cells was measured by flow cytometry (FIG. 5). These T cells were then co-cultured with infected resting CD4$^+$ T cells, without the addition of exogenous cytokines. IFN-γ from the supernatant was measured at day 3 (FIG. 6) and day 7 (FIG. 7) as a read-out for T cell clone recognition.

These data demonstrate that T pharmacytes carrying IL-15SA and IL-2 and IL-7 are capable of inducing HIV-expression from latently infected resting CD4$^+$ T cells, allowing for these same T pharmacytes to recognize these induced targets and mount an antiviral response.

Example 5

Nanoparticle Encapsulated IL-1 SSA Reverses HIV Latency

Figure 8:
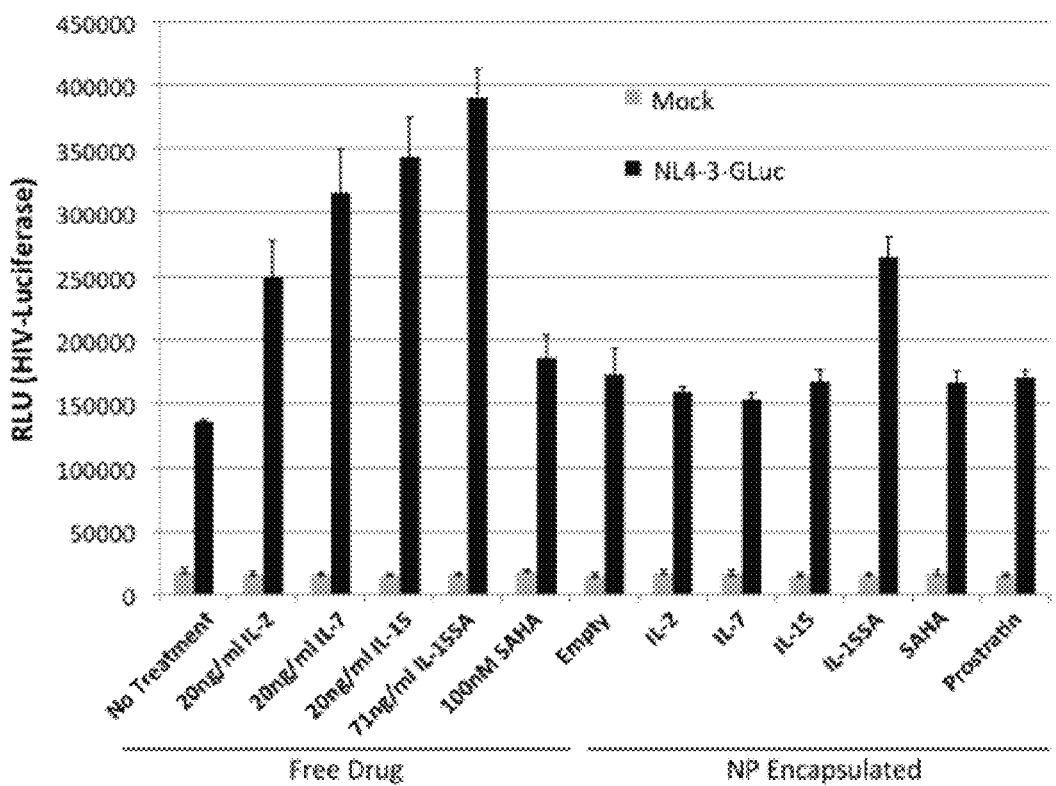
FIG. 8 shows a graph demonstrating that nanoparticle-encapsulated IL-15SA reverses HIV latency.

To investigate the effects of nanoparticle encapsulated IL-15SA on HIV latency, primary resting CD4$^+$ T-cells were treated with C-C motif chemokine 19 (CCL19) and then infected with a recombinant HIV virus encoding Gaussia luciferase or maintained as mock-infected controls. These cells were then treated with the indicated free drugs, or co-cultured with an autologous CMV-pp65-specific CD8$^+$ T-cell clone conjugated to interbilayer-crosslinked multilamellar vesicle (ICMV) nanoparticles encapsulating the indicated drugs for 79 hours. FIG. 8 presents a graph showing luciferase activity expressed as relative light units. An increase in luciferase expression correlates with HIV latency reversal. The data indicate that nanoparticle-encapsulated IL-15SA is effective for reversing HIV latency.

It appears, based on the comparative data of FIG. 8, that nanoparticle-encapsulated cytokine is not as effective as free cytokine. However, it is important to note that IL-15SA may be targeted to sites of HIV latency and is released from the nanoparticle over time, while the free drug, by comparison, may never reach the target site. Thus, nanoparticle-encapsulated cytokine may, in fact, be more effective than free cytokine at reversing HIV latency.

Example 6

Nanoparticle-encapsulated Anti-retrovirals (ARVs) Suppress HIV Replication

Figure 9:
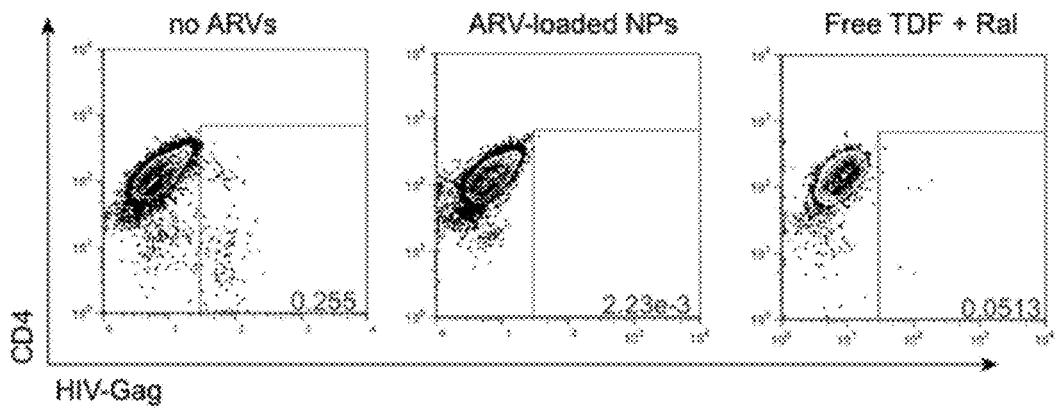
FIG. 9 shows graphs of flow cytometry analyses demonstrating that nanoparticle-encapsulated anti-retrovirals (ARVs) suppress HIV replication.

In some instances, for antiretroviral (ARV) drugs to be effective in vivo, they must reach suppressive concentrations in lymphoid tissue. To assess the suppressive effect of ARVs on HIV replication, ARV-loaded ICMV nanoparticles were generated by rehydration of lipid films with a solution containing tenofovir disoproxil fumarate (TDF), emtricitabine (FTC), and raltegravir (Ral). These were added at approximately $1 \times 10^8$ particles/ml to a culture of activated CD4$^+$ T-cells. Control conditions were setup with no ARVs or with TDF, FTC and Ral added as free drugs. For each condition, cells were then infected with HIV at an multiplicity of infection (MOI) of 0.01. 96 hours later, frequencies of infected cells were measured by flow cytometry staining for HIV-Gag (x-axis) and CD4 (y-axis). Results are shown in FIG. 9. The graph on the left shows activated control CD4$^+$ T-cells, the graph in the middle shows suppression by ARV-loaded nanoparticles, and the graph on the right shows suppression with free ARVs. Thus, the data demonstrates that nanoparticle-encapsulated ARVs suppress HIV replication.

Example 7

Figure 10:
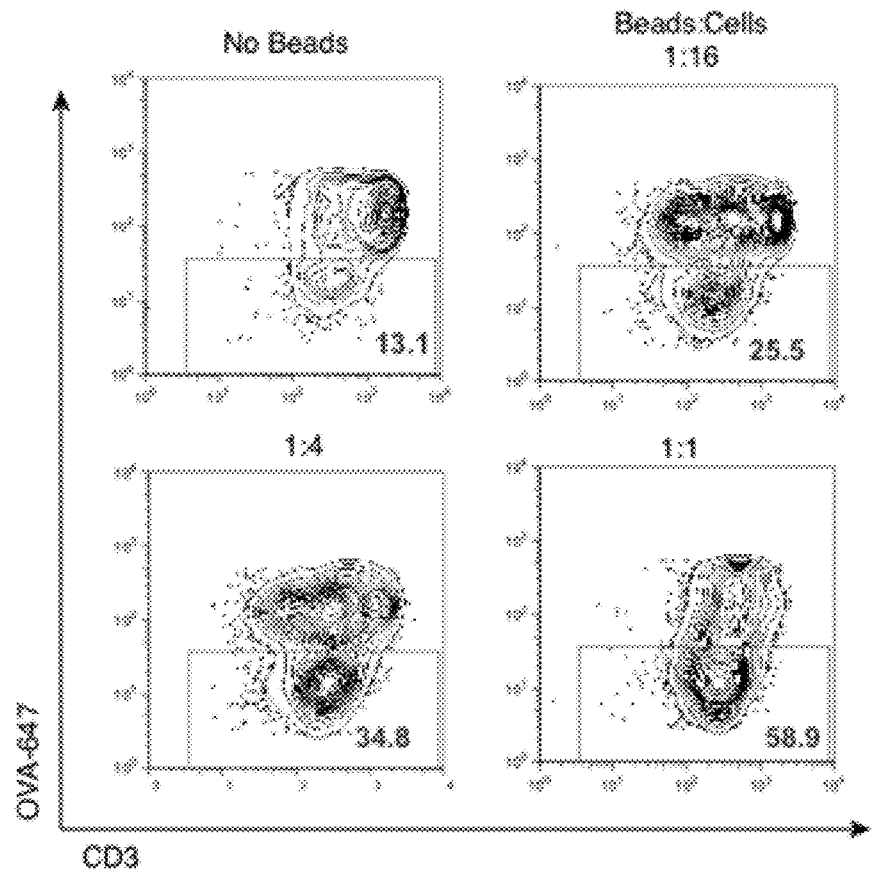
FIG. 10 shows graphs of flow cytometry analyses demonstrating that TCR stimulation triggers release of contents from T-cell conjugated nanoparticles.

TCR Stimulation Triggers Release of Contents from T-cell Conjugated Nanoparticles Natural killer cells and cytotoxic T lymphocytes kill virus-infected and neoplastic cells by releasing the pore-forming protein perforin and granzyme proteases from cytoplasmic granules into the cleft formed between the abutting killer and target cell membranes. To investigate whether release of nanoparticle contents results upon activation of T cells, a CMV-pp65-specific CD8$^+$ T-cell clone was conjugated to ICMV nanoparticles that had been loaded with Alexa-647 labeled ovalbumin (OVA). These "T-pharmacytes" were then co-cultured with anti-CD3/anti-CD28 beads (to activate T cells) at the indicated bead:cell ratio for 16 hours. Cells were then stained with a fluorochrome-conjugated anti-CD3 antibody. FIG. 10 shows flow cytometry plots depicting CD3 (x-axis) by OVA-Alexa-647 (y-axis). The data shown in FIG. 10 demonstrate that nanoparticle payload release is triggered by T cells.

Example 8

Triggering T-pharmacytes with Cognate Peptide Results in Release of Cargo

Figure 11:
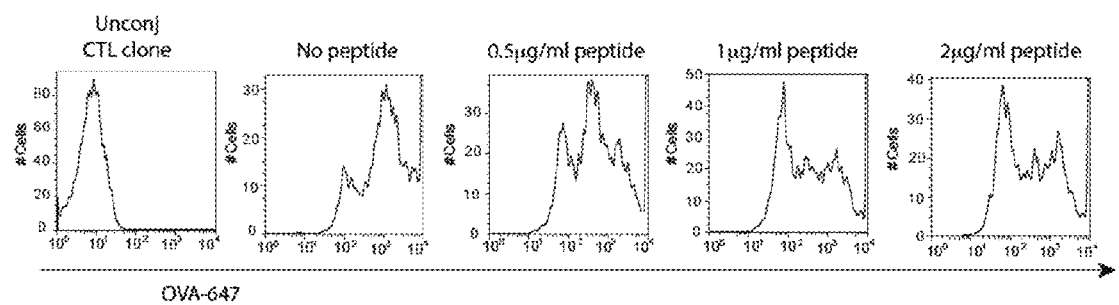
FIGS. 11A and 11B show graphs demonstrating that triggering T-pharmacytes with cognate peptide results in release of cargo.
Figure 11:
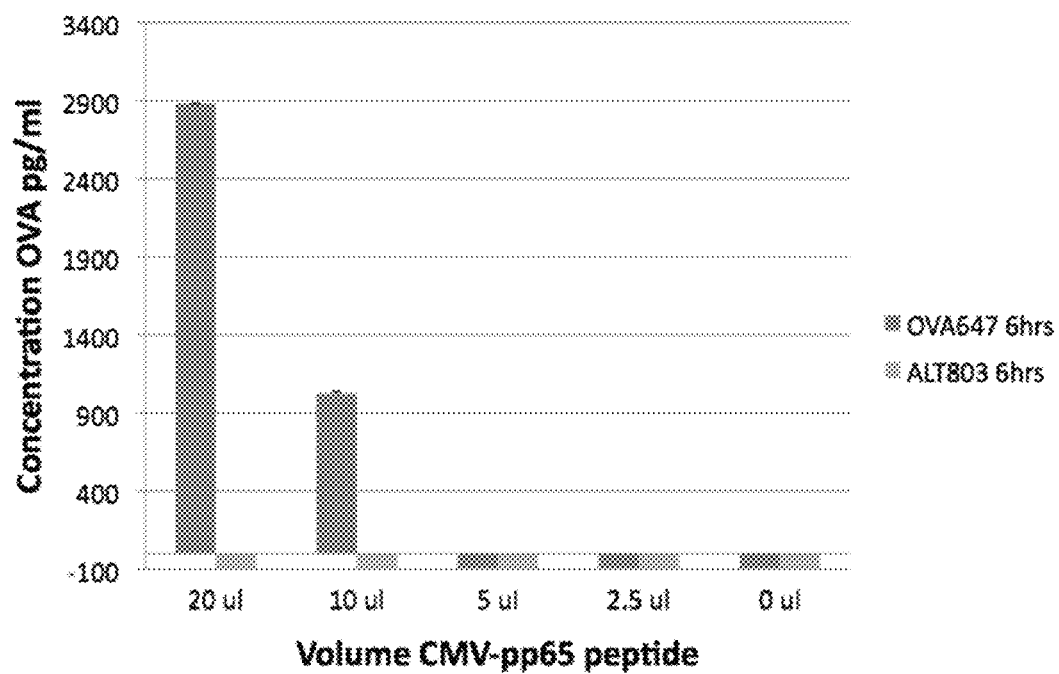

The above experiments relied on beads coated with antigen to trigger activation of T cells. The following experiments employ target cells containing antigenic peptide to stimulate T cell activation. A CMV-pp65-specific CD8$^+$ T-cell clone was conjugated to ICMV nanoparticles loaded with Alexa-647 labeled OVA. These cells were co-cultured with autologous BLCL plus the indicated concentrations of CMV-pp65-peptide pool for 16 hours. FIG. 11A shows histograms of flow cytometry data. In an experiment analogous to the foregoing, supernatants were collected following the 16 hour co-culture period, and the concentrations of non-cell-associated OVA were quantified by ELISA. The results of those experiments are shown in FIG. 11B. Increasing amounts of antigenic peptide correlated with increasing amounts of OVA payload released from the nanoparticles into the supernatant.

Example 9

Perforin is Sufficient to Trigger Release of Contents from ICMV Nanoparticles

Figure 12:
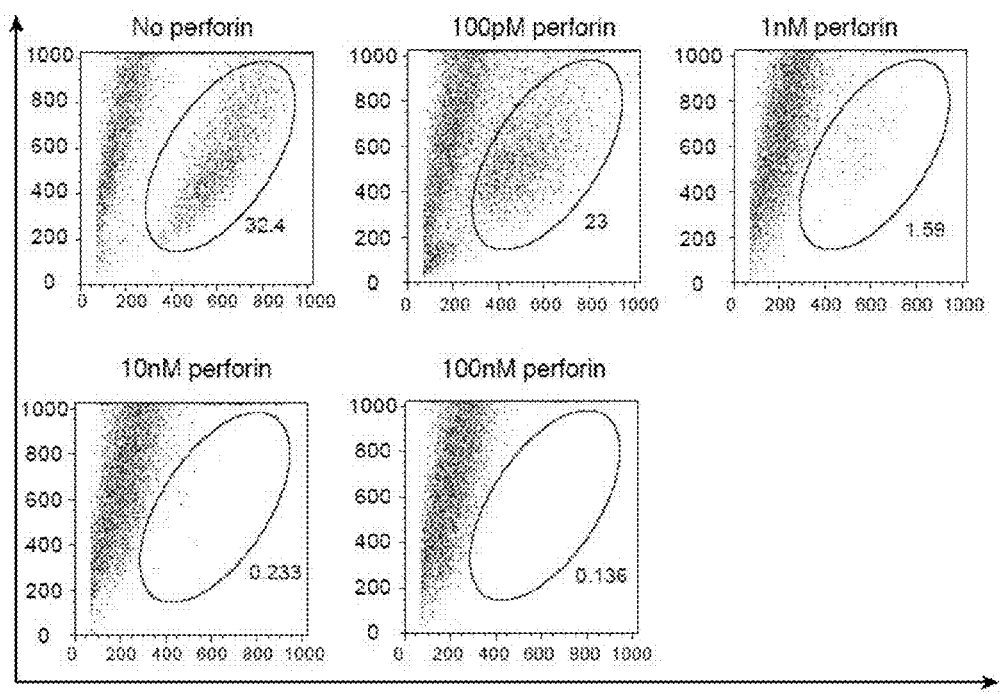
FIGS. 12A and 12B show graphs demonstrating that perforin is sufficient to trigger release of contents from interbilayer-crosslinked mulrilamellar vesicle (ICMV) nanoparticles.
Figure 12:
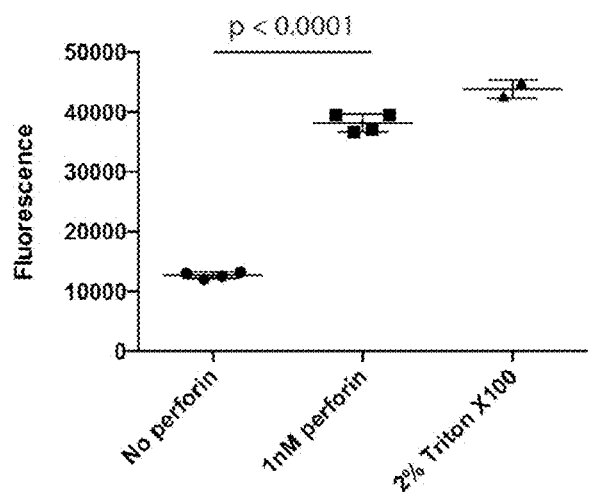

The next series of experiments were designed to test the effects of different concentrations of recombinant perforin on lysis of a B lymphoblastoid cell line (BLCL). FIG. 12A shows flow cytometry data indicating forward scatter-FSC (x-axis) by side scatter-SSC (y-axis). The cell populations with FSC/SSC characteristics of viable BLCL have been gated. 1 nM perforin appeared to be sufficient for clear cell lysis. To investigate whether perforin release from T cells is sufficient to trigger release of payload from nanoparticles conjugated to T cells, ICMV nanoparticles encapsulating Alexa-647-labeled OVA were treated with 1 nM perforin for 16 hours, or maintained as a no-treatment control. As a positive control for complete lysis, NPs were treated with 2% Triton X-100. Fluorescence was quantified at 647 nm absorbance and 695 nm emission. Results shown in FIG. 12B indicate that 1 nM perforin was sufficient to trigger release of OVA from ICMV nanoparticles.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is to deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements to other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for delivering IL-15 superagonist (IL-15SA) to Human Immunodeficiency Virus (HIV)-infected cells, including cells latently infected with HIV, the method comprising administering, to a subject having or suspected of having an HIV infection, a HIV-specific T cell bound to a nanoparticle that comprises IL-15SA in an amount effective to induce HIV expression from cells latently infected with HIV, wherein the agent is released from the nanoparticle in vivo.

2. The method of claim 1, further comprising administering to the subject antiretroviral therapy (ART).

3. The method of claim 1, wherein the HIV-specific T cell is autologous to the subject.

4. The method of claim 1, wherein the HIV-specific T cell is activated prior to administration to the subject.

5. The method of claim 1, wherein the HIV-specific T cell is naturally occurring.

6. The method of claim 1, wherein the HIV-specific T cell is genetically engineered.

7. The method of claim 1, wherein the nanoparticle is about 20-500 nm in diameter.

8. The method of claim 1, wherein the HIV-specific T cell is covalently bound to the nanoparticle.

9. The method of claim 1, wherein the HIV-specific T cell is bound to a plurality of nanoparticles.

10. The method of claim 9, wherein the HIV-specific T cell is covalently bound to the plurality of nanoparticles.

11. A T pharmacyte comprising a Human Immunodeficiency Virus (HIV)-specific T cell bound to a nanoparticle that comprises IL-15 superagonist (IL-15SA) in an amount effective to induce HIV expression from cells latently infected with HIV.

12. A composition comprising the T pharmacyte of claim 11.

13. A method comprising contacting a HIV-infected cell with the T pharmacyte of claim 11, wherein the IL-15SA is released from the nanoparticle.

14. The method of claim 7, wherein the nanoparticle is about 100-300 nm in diameter.

15. The method of claim 14, wherein the nanoparticle is about 150 nm in diameter.

16. The method of claim 1, wherein the nanoparticle is loaded with about 100 μml IL-15SA.

17. The method of claim 9, wherein the plurality of nanoparticles comprises about 50 to about 100 nanoparticles that each comprise IL-15SA.

18. The method of claim 1, wherein the nanoparticle is an interbilayer crosslinked multilamellar vesicles (ICMV).

19. A method for delivering IL-15 superagonist (IL-15SA) to Human Immunodeficiency Virus (HIV)-infected cells, the method comprising administering, to a subject having or suspected of having an HIV infection, a HIV-specific T cell bound to about 50 to about 100 nanoparticles, each nanoparticle comprising about 100 μg/ml IL-15SA, wherein the IL-15SA is released from the nanoparticle in vivo.

20. The method of claim 19, wherein the nanoparticles are interbilayer crosslinked multilamellar vesicles.

* * * * *